United States Patent [19]

Brown

[11] Patent Number: 4,949,840

[45] Date of Patent: Aug. 21, 1990

[54] SPECIMEN COLLECTION KIT FOR MAILING

[76] Inventor: J. Theodore Brown, 12214 Parkton Ct., Ft. Washington, Md. 20744

[21] Appl. No.: 448,231

[22] Filed: Dec. 11, 1989

[51] Int. Cl.$^5$ .................... B65D 81/04; B65D 81/14
[52] U.S. Cl. ........................ 206/204; 53/449; 206/522; 206/523; 206/569; 604/317
[58] Field of Search ................ 53/449; 206/204, 232, 206/521–523, 529, 569, 588, 591, 592, 594; 604/317

[56] References Cited

U.S. PATENT DOCUMENTS

| | | | |
|---|---|---|---|
| 1,965,227 | 7/1934 | Fiero | 206/521 |
| 2,897,641 | 8/1959 | Simon et al. | 53/449 |
| 3,349,990 | 10/1967 | Woodford | 206/521 |
| 3,435,946 | 4/1969 | Sobek et al. | 206/523 |
| 3,460,740 | 8/1969 | Hagen | 206/523 |
| 3,868,056 | 2/1975 | Keren | 206/521 |
| 3,893,280 | 7/1975 | King | 53/449 |
| 3,948,436 | 4/1976 | Bambara | 206/523 |
| 4,240,547 | 12/1980 | Taylor | 206/523 |
| 4,560,069 | 12/1985 | Simon | 206/523 |
| 4,620,633 | 11/1986 | Lookholder | 206/523 |
| 4,679,688 | 7/1987 | Soderhold | 206/521 |
| 4,793,123 | 12/1988 | Pharo | 53/449 |
| 4,882,893 | 11/1989 | Spencer | 53/449 |
| 4,884,684 | 12/1989 | Bernardin et al. | 206/523 |

Primary Examiner—Jimmy G. Foster
Attorney, Agent, or Firm—Clay Holland, Jr.

[57] ABSTRACT

A combination clinical specimen collection vial and shipping means, including packaging components, are provided, which are uniquely adapted and acceptable for shipment and delivery through regular first-class mailing-delivery systems, for both domestic and overseas purposes.

13 Claims, 2 Drawing Sheets

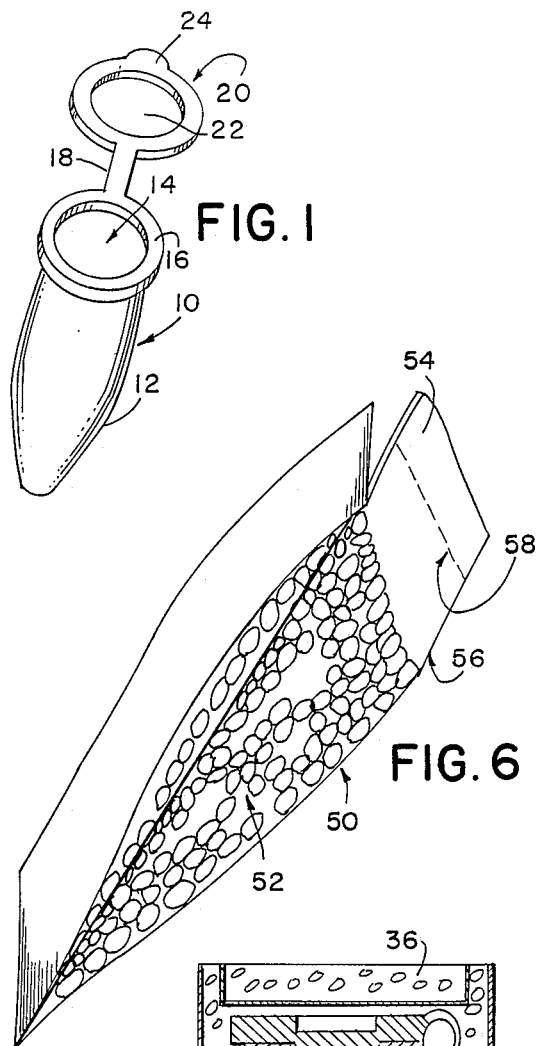
FIG. 1
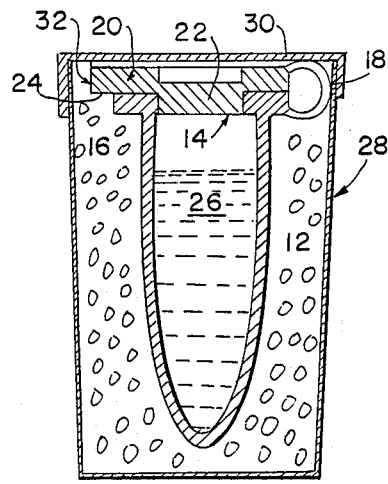
FIG. 2
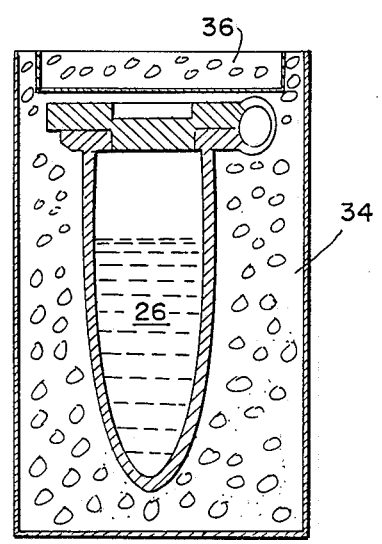
FIG. 3
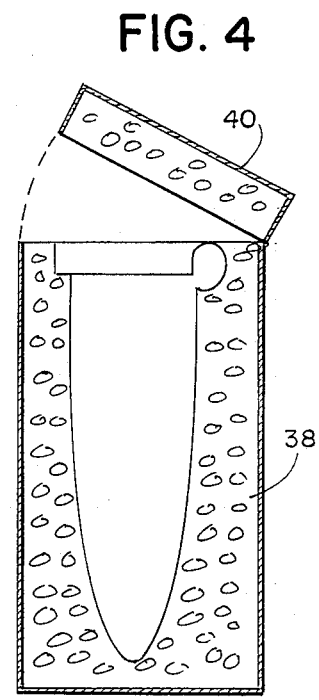
FIG. 4
FIG. 6

SPECIMEN COLLECTION KIT FOR MAILING

FIELD OF THE INVENTION

The present invention related to the field of drug abuse screening and laboratory testing, and more particularly to individual clinical specimen collection kits for mailing liquid samples or specimens of body fluids, such as urine, through the regular U.S. mail service system from points of origin to remote laboratory test and analysis facilities.

BACKGROUND OF THE INVENTION

In the prior art, hospitals, clinics and doctors, etc. have routinely taken various samples or specimens of patient's blood, urine or stool and the like, to be sent for testing and analysis by an outside remote laboratory. Such specimens must be transported and delivered promotely to such laboratories by means which will not cause damage or spillage thereto. Present widely employed delivery packages may include a glass test tube or plastic vials as containers for such specimen collection. Once closed the container is deposited in a small cardboard cylindrical packaging/delivery tube, usually no larger than ½ inch to 2 inches in diameter and no longer than 6 inches. Generally, the inserted container is loosely surrounded by various types of packaging materials, such as newspaper, foam rubber, etc. for the purpose of inhibiting the container's movement within the cardboard tube. The cardboard tube may have metal end pieces or metal screw-on caps to retain the container within the packaging tube.

Such a package ready for transport and delivery is rather weighty and bulky, and costly for shipment via the regular first-class U.S. mail service system, and therefore is undesirable for mass or individual mailings as may be required in connection with extensive mailings associated with various drug testing programs which have impact on a significant percentage of the nation's current population.

Recently the Supreme Cout of the United States has ruled that transportation operators, such as railroads, airlines, buses, and the like may require testing for drug abuse of its employees. In addition, many employers have instituted private programs for testing their employees. Further, many parents have expressed concern about the widespread use by school age children and many have expressed a desire for individual means whereby they could test and monitor whether their children are involved in any drug abuse activities.

It is difficult to predict how extensive the need or desire for such drug testing will grow. However, one thing is certain: drug abuse has reached into almost every area of business and society of this nation. Thus, private industry, governmental agencies and private individuals alike, have serious concerns and will seek the assistance of various testing and evaluation laboratories to analyze samples and specimens for drug abuse on an ever expanding basis.

As a consequence of the anticipated escalation in the volume of packages which may be required or desirable to be sent through the mail service system, it has therefore become paramount to provide a lightweight and inexpensive transport and delivery package adapted and acceptable for use in mailing body fluid specimens to remote laboratories for drug testing and analysis, which is cost effective.

The prior art packaging and process shipping and delivery via the current mail service system have several undesirable features either singularly or in combination: namely, that there are no mechanical or structural means immediately surrounding the specimen carrying container to insure that the plug or cap of said vial will not become unplugged; nor is there provided specific means for absorption of fluid specimen in the unlikely event of the leakage or rupture of the container; nor is there provided further shock absorption means to minimize, if not eliminate, damage to the specimen carrying container in transit; and last and more importantly, the complete shipping and delivery package of the prior art is not an economical and cost effective means in view of the significantly high cost of shipping, both domestically and overseas, via the current first-class mail service system, which is used for prompt delivery of such test specimens.

Therefore, it is an object of the present invention, to provide shipping and delivery package and process which is economical, i.e. less than one-half cost of first-class mail for prior art devices and processses for specimens of equal size and weight.

Another object is to provide absorptive means within the packaging for absorption of the fluid specimen in the unlikely event of spillage.

Yet another object of the present invention is to provide a packaging combination which is uniquely acceptable to the current first-class serivce system, for both domestic and overseas shipment.

While another object of the invention is to provide absorptive shock and pressure protection means to the specimen container during its transit through the current mail service system.

BRIEF SUMMARY OF THE INVENTION

In accordance with the preferred embodiment of the present invention, there is provided a clinical sample or specimen collection container and packaging for shipment and delivery which are uniquely adapted and acceptable for handling over long distances utilizing the U.S. commercial mail services system. More specially, a miniature size plastic vial having a tight fitting plug-like cap connected thereto, which is employed to plug the via air tight, for retaining a liquid contained therein. The vial is snugly fitted into a block of polyethylene, having a spongy-like cushion texture, such that the top of the vial and its plug-like cap are slightly depressed into the block below an adjacent top surface of the block and then held firmly in place by a piece of adhesive tape or other covering means over the top of the vial, to further insure that the vial will not come unplugged. With the vial snugly fitted into the cushion block of polyethylene, it is then placed into an absorptive pouch-like member and sealed; these combined packaging components are finally inserted into a lightweight mailing enclosure or envelope having a complete inner-lining of air-bubble filled packaging material, which is sealed and ready for mailing.

The unique combination is now ready for transport and delivery via the current mailing service system, for domestic and overseas, mailing. Mailing of a specimen in accordance with this embodiment of the invention is safe, economical and acceptable by the mail service system for expeditious delivery.

BRIEF DESCRIPTION OF THE DRAWINGS

FIG. 1 is a perspective view of a small clinical plastic specimen collection vial showing a plug-like cap connected at the mouth thereof;

FIG. 2 is a cross-sectional view of the vial shown in FIG. 1, which is closed at top and snugly fitted into a cushion block of polyethylene and held in place by a piece of adhesive tape over the top of the vial and block;

FIG. 3 is a cross-sectional view of another embodiment of the cushion block shown in FIG. 2, having a top plug for covering the vial top;

FIG. 4 is another cross-sectional view of a cushion block of the type shown in FIGS. 2 and 3, where the cushion block has a lift-up lid for covering the top of the vial;

FIG. 6 is a perspective view of a mailing enclosure or envelope having a full air-bubble lining material herein into which the combination of parts are deposited and sealed.

DETAIL DESCRIPTION OF THE INVENTION

Figures 5, 7:
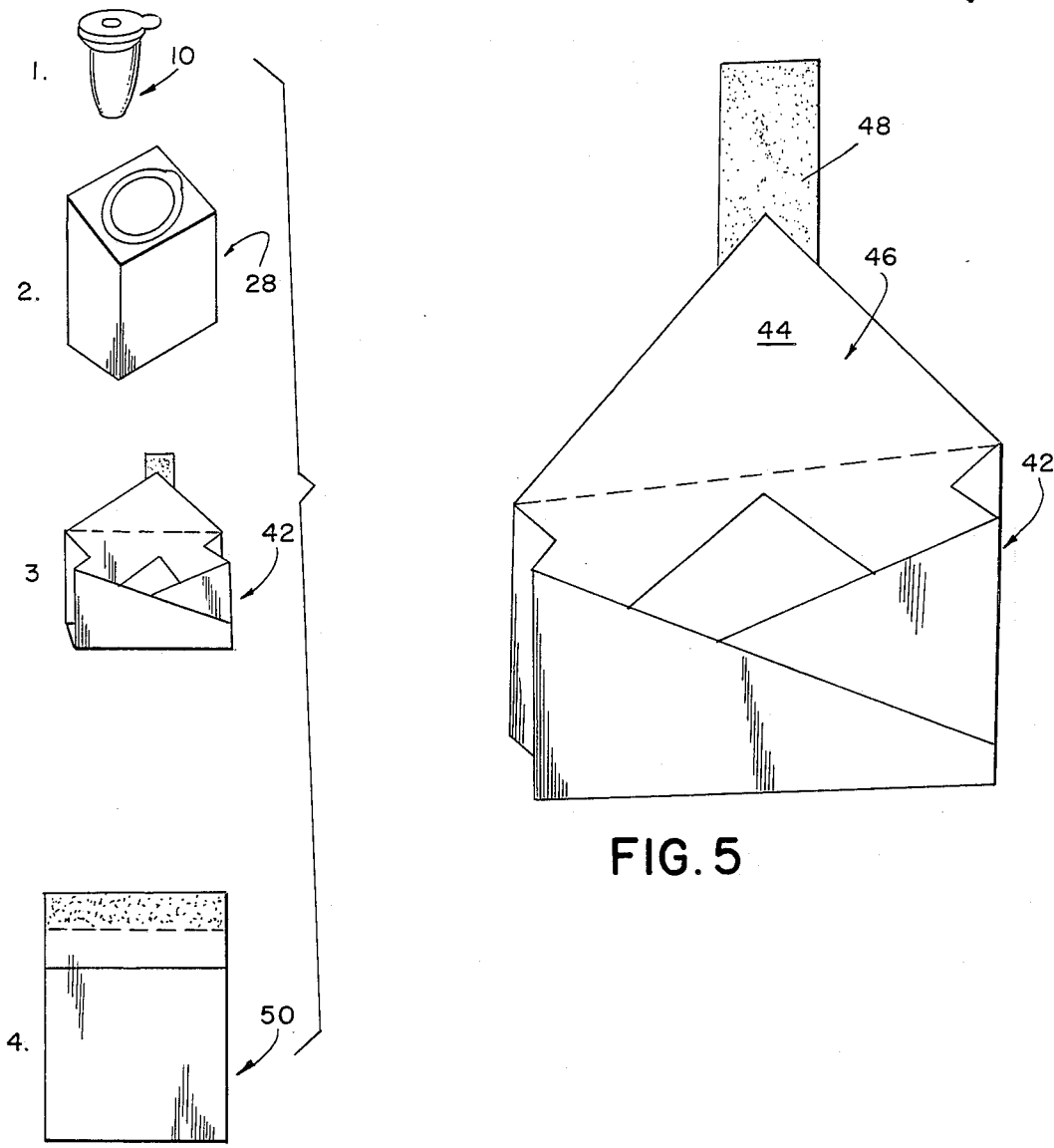
FIG. 5 is a perspective view of an absorptive lightweight pouch, into which the vial and block are placed.
FIG. 7 is a diagram illustrating the sequence of steps through which a specimen collection vial flows to form a completed clinical collection kit ready for mailing in the current mail service system.

In FIG. 1, there is shown a small plastic body fluid specimen collection container 10 or vial, having a body 12 of a bullet-like configuration and having a tube opening 14 and lip 16. Connected to lip 16 is a thin connecting member 18, which is in turn connected to a plug-like cap 20, having a plug extended portion 22 and lip portion 24. In this representative embodiment of container 10 for specimen collection, the unit may be of plastic material. In addition, although the container or vial, as such containers are sometimes called, is shown as having a bullet-like configuration, but may have a variety of configurations while remaining within the scope and spirit of the present invention.

Referring now to FIG. 2, there is shown a cross-sectional view of vial 10 with its plug-like cap 20 firmly locked in opening 14 to thereby retain a fluid 26 contained therein. The closed vial is snugly fitted into a rectangular cushion block of material 28 and has a strip of adhesive tape 30 overlapping the top of block 28 and cap 20, to thereby hold vial 10 snugly fitted in place. Block 28 is in the form of a foam-like cushion or sponge-like material and may be made of foamed polyethylene material.

The function of block 28 is to provide jar or shock resistance protection for container 10 during transport and delivery through the regular mail/postal service system. As shown in FIG. 2, cap 20 is depressed slightly into block 28 below the top thereof, by a distance illustrated by reference numeral 32. Such a depressed position provides additional protection to the container to withstand shock and to insure that cap 20 does not come out of opening 14, to thereby avoid spillage of fluid 26 contained therein.

It should be noted at this point that tube 10 depicted in this representative embodiment of the invention, is commonly known as an "Effendorf Tube" and is not known in the art to be used as a collection tube as disclosed and taught herein. Traditionally, the Effendorf tube is used in selected laboratory analysis work, for which it was apparently originally designed. Consequently, the use of such a tube in accordance with the present invention, is clearly not obvious, and is to be considered new and useful and unobvious in the context of the present invention.

Continuing with the description of the present invention, FIGS. 3 and 4, illustrate two different embodiments for block 28, namely, block 34 in FIG. 3 has a plug 36, which functions to secure the position of container 10 within block 34; block 38 in FIG. 4, has a hinged or lift-up lid 40 which provides a similar function. Both of these configurations tend to prove adequate for the design functions intended, i.e., providing means for retaining container 10 snugly in place and to provide both lateral and axial resistance protection from jar and shock forces to the package in the combination. Additional protection insurance is provided by the use of a strip of adhesive tape 30 as depicted in FIG. 2, to cover plug 36 or lid 40, in FIGS. 3 and 4, respectively.

Referring, now to FIG. 5, there is shown an absorptive pouch 42, which has a flap 44 deliniated by a broken-line 46; when folded down along broken-line 46, flap 44 closes pouch 42 and the use of an adhesive strip 48 may be employed to seal the pouch.

The kit packaging combination and process is continued by inserting sealed block 28 and container 10 into pouch 42, which is in turn also sealed with strip 48.

In FIG. 6, there is shown a mailing envelope 50 in perspective view, illustrating its inner-lining 52, which consists of a thin plastic material having a plurality of small air-bubble pockets, to thereby provide a cushioned interior for objects contained therein. Envelope 50 has an adhesive lip area 54 and a flap 56 used to close and seal the envelope when flap 56 is folded down along a broken-line 58 of flap 56.

As a final step to the completion of the kit packaging combination and process, sealed pouch 42 containing block 28 and container 10 are inserted into envelope 50 and sealed close by flap 56 and adhesive area 54.

A complete step-by-step understanding of the combination of kit components and packaging process is more fully depicted in FIG. 7, where a representative embodiment of the various components of the present inventive combination and packaging method are presented.

As shown in FIG. 7, the method for packaging the kit is depicted in four steps. Upon completion of these four steps the fluid specimen collection container is complete and ready for transport and delivery via regular mail/postal service.

Further disclosure of the present invention is made with reference to an example, as follows:

EXAMPLE

This exemplary example of the disclosed kit is uniquely useful and adaptable for individual use, such as parents of school age children, who may be interested in ascertaining and periodically monitoring whether their specific child or children are involved in drug abuse. In order to facilitate such a desire and determination in a confidential manner, the parent is able to do so by utilizing the testing and analysis services of existing or future established laboratories set up for such purposes with the aid of the specimen collection kit disclosed herein and a simple set of written instructions for easy use and assemblage for mailing.

At least one known commercial laboratory offers a testing and analysis service responsive to such parents or any individual of the general public sector on a confidential or anonymous basis. In order to provide such services on an inexpensive and cost effective basis, it was necessary to devise a cost effective means for transport and delivery of a body fluid, such as a urine specimen, through the regular mail/postal service system, in sufficient quantity to permit completion of appropriate tests and analysis, deliverable from the place of origin to a remotely located laboratory facitliy, promptly and conveniently.

It is known by those versed in the laboratory testing and analysis business, that on the order of less than 60 milliliters of urine is required to perform drug abuse tests for marijuana, opiates, cocaine, PCP and amphetamines, and other substances of abuse. Thus, the problem to be overcome was that of conceiving of means for transport and delivery of such a small quantity of body fluid, which can be promptly and safely delivered and which is acceptable for transport through the nation's regular mail/postal service system.

In this example, it has been found that the use of a container 10 which is on the order of greater than 60 millimeters in volumetric capacity of lightweight plastic with a safe closure cap, such as cap 16, is uniquely adaptable for the desired use and solution in a specimen collection kit. This is especially so when the container is packaged in an acceptable manner as disclosed and taught herein.

However, in order to meet the other requirements for acceptability by the regular mail/postal service, it was necessary to develop and design means for protecting the container 10 from any adverse shock of jarring or impact to the container and its contents while in transit. After considerable investigation and testing, the means developed was cushion blocks 28, 34, and 38, into which container 10 is snugly fitted to provide protection along three mutually perpendicular axes. Next it was necessary to devise and select an appropriate light weight and acceptable means for absorption of fluid 26, in the unlikely event of its spillage; the next development was that of pouch 42 which is also lightweight and provides the adequate and acceptable protection needed. Finally an outer enclosure for actual mail processing was needed and envelope 50 evolved and was selected after appropriate investigation and testing, because of its light weight and acceptability by the mail/postal service as a recognized mailing envelope currently known and used in the industry to accommodate the transport and delivery of a wide range of items by the mail/postal service.

It should be noted that in this present example, vial 10 is filled with body fluid to only above seventy-five percent of its volumetric capacity. The void provided within container 10 by only partial filling of container 10 eliminates any possible pressure build-up within from being developed. Thus, any axial pressure build-up against cap 20 is avoided along with the possibility of such pressure build-up causing cap 20 to be dislodged.

As can readily be seen and appreciated from the present disclosure and teachings herein, the present invention provides a new, useful and unobvious combination and packaging method for a fluid body specimen collection kit which is cost effective owing to its light weight and its ability to withstand the abuses encountered in transit through the mail/postal service system. Further, its usefulness is exemplified by the fact that the kit of cooperative components can be readily assembled by individuals of the general public with minimal written instructions. In addition to being acceptable to the mail/postal service, for both domestic and overseas delivery, the cost for delivery via regular first-class mail service is substantially less than the cost of delivery of known prior art devices or methods where prompt delivery is needed.

It is to be understood, that the above embodiment set forth in the example, wherein the body fluid used was urine, is only illustrative of the various types of body fluids which may be sent through the mail/postal system utilizing the kit of the present invention. More particularly, specimens, such as blood, semen, etc. for humans and other animals may be collected and sent via the delivery kit disclosed, with all the advantages attendent therewith. Further, it is to be understood that other modifications or adaptions may occur which would fall within the spirit and scope of the invention. For example, the invention encompasses glass for container 10 of other configurations therefor. Therefore, all such modifications or variations, are intended to be included within the scope and spirit of the invention as defined in the appended claims and disclosure.

What is claimed as new is:

1. An improved method for packaging a collected specimen of animal body fluid for mailing via regular mail service system, said improvement comprising the steps of:
    a. partially filling a specimen collection container having a predetermined volume capacity, with an animal body fluid in an amount equal to at least three quarters of said container's volume capacity;
    b. sealing said partially filled container with a plug-like cap for retaining said body fluid therein;
    c. snugly fitting said sealed container into a block of cushion-like material to reduce the shock of a jar or impact to said container;
    d. securing said snugly fitted sealed container and block of cushion material by a flexible retainer means;
    e. enclosing said block of cushion material with said sealed container therein, in a pouch of absorptive material and sealing said pouch;
    f. enclosing said pouch containing said block and container in a mailing envelope having a complete air-bubble material inner-lining, and sealing said envelope, to thereby complete a light weight package which is safe and acceptable for transport and delivery by regular mail service system.

2. Method of claim 1, in which said specimen collection container is glass or plastic tube.

3. Method of claim 2, in which said plastic tube has a bullet-like shape.

4. Method in claim 2, in which said container has a volume capacity greater than 60 milliliters.

5. Method in claim 1, in which said body fluid is blood, urine or semen.

6. Method in claim 1, in which said cushion material is polyethylene foam with air voids therein.

7. Method in claim 1, in which said means for securing said container within said block is an adhesive strip of tape, a 8. Method in claim 1, in which said pouch is lightweight paper.

9. An improved animal body fluid specimen collection kit for mailing via regular mail service system, said improvement comprising:
    a. a specimen collection container having a predetermined volume capacity, and a plug-like cap connected at an end and opening of said container, to thereby retain a fluid therein when said cap is placed in said opening;

b. a block of cushion material for snugly receiving said entire volume capacity of said container, to thereby reduce the shock of a jar or impact to said container;

c. means for securing said container within said block of cushion material;

d. a pouch of absortive lightweight material for receiving said container and block, to thereby provide means for absorbing fluid from said container in the event of spillage; and e. a mailing envelope having a complete air-bubble inner-lining of material, to further reduce the shock of a jar or impact to said container during the transport and delivery via regular mailing.

10. A collection kit as in claim 9, in which said body fluid is blood, urine or semen.

11. A collection kit as in claim 9, in which said cushion material is polyethylene foam material.

12. A collection kit as in claim 9, in which said means for securing said container within said block is a strip of adhesive tape, cushion plug or lift-up lid.

13. A collection kit as in claim 9, in which said pouch is absorptive light weight paper.

* * * * *